US010422763B2

(12) United States Patent
Hidaka et al.

(10) Patent No.: US 10,422,763 B2
(45) Date of Patent: Sep. 24, 2019

(54) DIELECTRIC CONSTANT MEASUREMENT METHOD FOR POWDER IN POWDER-DISPERSED COMPOSITE MATERIAL

(71) Applicant: SHIRAISHI KOGYO KAISHA, LTD., Osaka, Osaka (JP)

(72) Inventors: Jusuke Hidaka, Amagasaki (JP); Kizuku Kushimoto, Sendai (JP)

(73) Assignee: SHIRAISHI KOGYO KAISHA, LTD., Osaka (JP)

( * ) Notice: Subject to any disclaimer, the term of this patent is extended or adjusted under 35 U.S.C. 154(b) by 0 days.

(21) Appl. No.: 15/766,136

(22) PCT Filed: Oct. 13, 2016

(86) PCT No.: PCT/JP2016/080322
§ 371 (c)(1),
(2) Date: Apr. 5, 2018

(87) PCT Pub. No.: WO2017/065198
PCT Pub. Date: Apr. 20, 2017

(65) Prior Publication Data
US 2018/0284173 A1  Oct. 4, 2018

(30) Foreign Application Priority Data
Oct. 15, 2015 (JP) .................. 2015-203594

(51) Int. Cl.
*G01N 27/22* (2006.01)
*G01R 27/26* (2006.01)
*G01N 33/00* (2006.01)

(52) U.S. Cl.
CPC ....... *G01N 27/221* (2013.01); *G01R 27/2605* (2013.01); *G01R 27/2617* (2013.01); *G01N 2033/0091* (2013.01)

(58) Field of Classification Search
CPC .................. G01N 27/221; G01R 27/2617
See application file for complete search history.

(56) References Cited

U.S. PATENT DOCUMENTS

| 5,451,882 A | 9/1995 | Wakino et al. |
| 2004/0246079 A1 | 12/2004 | Ehata |

(Continued)

FOREIGN PATENT DOCUMENTS

| JP | 52-85864 A | 7/1977 |
| JP | 2006-184209 A | 7/2006 |

(Continued)

OTHER PUBLICATIONS

Notification of Transmittal of Translation of the International Preliminary Report on Patentability (Form PCT/IB/338) issued in counterpart International Application No. PCT/JP2016/080322 dated Apr. 26, 2018, with Forms PCT/IB/373 and PCT/ISA/237. (7 pages).

(Continued)

*Primary Examiner* — Noam Reisner
(74) *Attorney, Agent, or Firm* — Westerman, Hattori, Daniels & Adrian, LLP (57) ABSTRACT

A method for measuring the relative dielectric constant of powder in a powder-dispersed composite material. A composite material is assumed as a cell combination in which unit cells having the same length a in each of an x-axis direction, a y-axis direction, and a z-axis direction are combined together and which has a length l in the x-axis direction, a length m in the y-axis direction, and a length n in the z-axis direction, each of the unit cells of the cell combination is considered to be constituted by a single powder element or a single medium element, the cell combination is created in which the powder element or the medium element is assigned to each of the unit cells in consideration of the number-based median particle diameter (Continued)

$D_{50}$, the maximum diameter $D_{max}$, the minimum diameter $D_{min}$, and the geometric standard deviation $\sigma_g$.

3 Claims, 7 Drawing Sheets

(56) References Cited

U.S. PATENT DOCUMENTS

2005/0093555 A1* 5/2005 Ehata ............... G01N 22/00 324/672
2009/0261847 A1* 10/2009 Petrovsky ......... G01N 27/026 324/663

FOREIGN PATENT DOCUMENTS

| JP | 2008-157840 A | 7/2008 |
| JP | 2014-13228 A | 1/2014 |

OTHER PUBLICATIONS

Hidaka, "Powder Simulation Supporting the Progress of Powder Technology", Funtai Gijutsu, Dec. 1, 2010, vol. 2, No. 12, pp. 15-21, cited in ISR of PCT/JP2016/080229 (7 pages total).

Kushimoto et al., "Yudenritsu ni yoru Biryushi Composite Zairyochu no Biryushi Bunsan Jotai no Keisoku", Society of Powder Technology, Japan Kenkyu Happyokai Koen Ronbunshu, Oct. 8, 2013, vol. 2013 Shuki, pp. 100-101, cited in ISRs of PCT/JP2016/080229 and PCT/JP2016/080322 (6 pages total).

Moriyama et al., "Relationship between Indices of Dispersibility of Filler Particles Obtained by Image Analysis and Characteristics of Composite Materials Contained Filler Particles", Preprint of the Symposium on Powder Science and Technology, Sep. 28, 2015, vol. 53, pp. 139-143, cited in ISR of PCT/JP2016/080229 (7 pages total).

International Search Report dated Jan. 10, 2017, issued in International Application No. PCT/JP2016/080229 (2 pages).

International Search Report dated Jan. 10, 2017, issued in counterpart International Application No. PCT/JP2016/080322 (2 pages).

Extended (supplementary) European Search Report dated Apr. 9, 2019, issued in counterpart EP Application No. 16855451.7. (7 pages).

Extended (supplementary) European Search Report dated Jun. 12, 2019, issued in counterpart EP Application No. 16855419.4. (7 pages).

* cited by examiner

DIELECTRIC CONSTANT MEASUREMENT METHOD FOR POWDER IN POWDER-DISPERSED COMPOSITE MATERIAL

TECHNICAL FIELD

The present invention relates to methods for measuring the dielectric constant of powder in a powder-dispersed composite material.

BACKGROUND ART

As methods for measuring the relative dielectric constant of powder itself, various measurement methods are known, such as the coaxial probe method, the transmission line method, the free-space method, the cavity resonator method, and the parallel plate capacitor method. Furthermore, Patent Literature 1 proposes a method for measuring the relative dielectric constant of powder itself using a slurry made of powder and a liquid.

CITATION LIST

Patent Literature

Patent Literature 1: JP-A-2008-157840

SUMMARY OF INVENTION

Technical Problem

However, there has been no known method for measuring the relative dielectric constant of powder in a powder-dispersed composite material in which the powder is dispersed in a medium, such as a polymeric material. Given that, strictly speaking, the relative dielectric constant of powder in a powder-dispersed composite material varies depending on a medium forming the matrix, there is a need to measure the relative dielectric constant of powder in the powder-dispersed composite material. Furthermore, there has been no established method for measuring the relative dielectric constant of surface-treated powder.

An object of the present invention is to provide a method for measuring the relative dielectric constant of powder in a powder-dispersed composite material.

Solution to Problem

A dielectric constant measurement method according to the present invention is a method for measuring a dielectric constant of powder in a powder-dispersed composite material containing the powder dispersed in a medium and includes: measuring a number-based median particle diameter $D_{50}$, a maximum diameter $D_{max}$, a minimum diameter $D_{min}$, and a geometric standard deviation $\sigma_g$ in a particle diameter distribution of the powder in an unagglomerated state; measuring a relative dielectric constant of the powder-dispersed composite material, a volume content Va % of agglomerates in the whole powder of the powder-dispersed composite material, and an average number Na of primary particles forming the agglomerates; assuming the powder-dispersed composite material as a cell combination in which unit cells having the same length a in each of an x-axis direction, a y-axis direction, and a z-axis direction are combined together in the x-axis direction, the y-axis direction, and the z-axis direction and which has a length l in the x-axis direction, a length m in the y-axis direction, and a length n in the z-axis direction; considering that each of the unit cells of the cell combination is constituted by a single powder element or a single medium element, and creating the cell combination in which the powder element or the medium element is assigned to each of the unit cells in consideration of the number-based median particle diameter $D_{50}$, the maximum diameter $D_{max}$, the minimum diameter $D_{min}$, and the geometric standard deviation $\sigma_g$ in the particle diameter distribution and a content of the powder in the powder-dispersed composite material; and assuming the cell combination as a laminate in which layers having a thickness d in the z-axis direction are combined and layered in the z-axis direction, and determining a relative dielectric constant of the powder in the powder-dispersed composite material from a relational expression of a relative dielectric constant $\varepsilon_{Total}$ of the cell combination determined by assigning a capacitance $C_{Layer,h}$ of each of the layers represented by Formula 1 below to Formula 2 below and a measured value of the relative dielectric constant of the powder-dispersed composite material.

[Math. 1]

$$C_{Layer,h} = \left\{ \sum_{j=1}^{\lfloor m/a \rfloor} \sum_{i=1}^{\lfloor l/a \rfloor} \left( \sum_{k=1}^{\lfloor d/a \rfloor} \frac{1}{\varepsilon_{ijk}\varepsilon_0 a} \right)^{-1} \right\}^{-1} \quad \text{Formula 1}$$

$\varepsilon_0$: dielectric constant of vacuum (F/m)

[Math. 2]

$$\varepsilon_{Total} = \frac{1}{\varepsilon_0} \cdot \frac{n}{lm} \cdot \left( \sum_{h=1}^{\lfloor n/d \rfloor} C_{Layer,h} \right)^{-1} \quad \text{Formula 2}$$

In the present invention, the length a of the unit cell is preferably $a=(D_{50}/\beta\sigma_g)$ and a fitting parameter $\beta$ thereof is preferably selected within a range of values where determination results of the relative dielectric constant $\varepsilon_{Total}$ have a constant standard deviation or within a range of values where variations in calculated volume content of the powder are sufficiently small.

In the present invention, the powder to be measured in terms of relative dielectric constant may be surface-treated powder.

Advantageous Effects of Invention

The present invention enables the measurement of the relative dielectric constant of powder in a powder-dispersed composite material containing the powder dispersed in a medium. The present invention also enables the measurement of the relative dielectric constant of surface-treated powder.

DESCRIPTION OF EMBODIMENTS

Hereinafter, a description will be given of a preferred embodiment. However, the following embodiment is merely illustrative and the present invention is not limited by the following embodiment.

Figure 1:
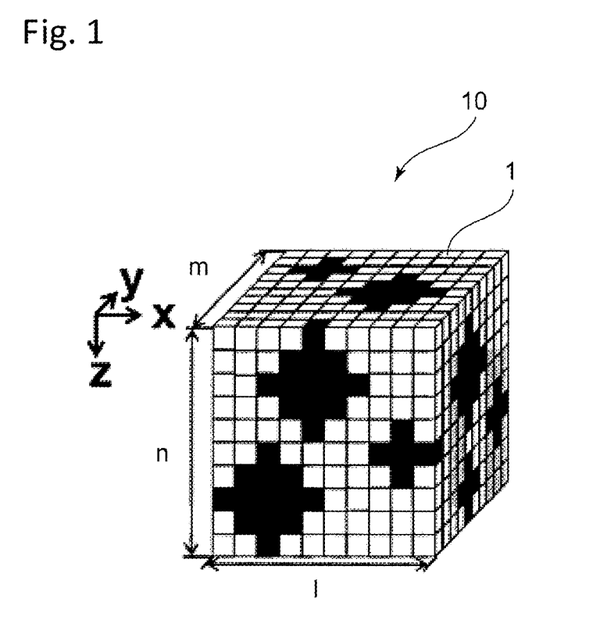
FIG. 1 is a perspective view for illustrating a cell combination assumed in the present invention.

FIG. 1 is a perspective view for illustrating a cell combination assumed in the present invention. In a method for measuring a dielectric constant according to the present invention, a powder-dispersed composite material is assumed as a cell combination 10 shown in FIG. 1. In the present invention, the powder-dispersed composite material is a composite material in which powder of an inorganic filler, an organic filler or others is dispersed in a medium, such as a resin or a polymer.

Figure 3:
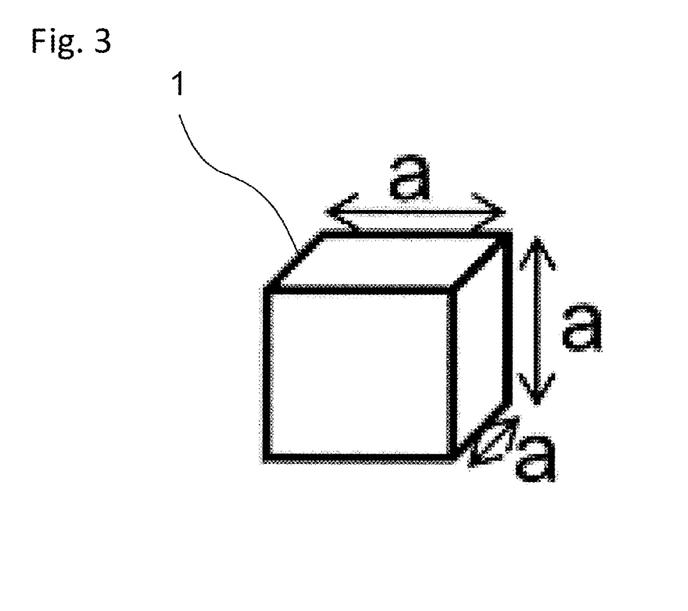
FIG. 3 is a perspective view showing a unit cell constituting part of the cell combination in the present invention.

The cell combination 10 shown in FIG. 1 is formed by combining unit cells 1 shown in FIG. 3 together in the x-axis direction, the y-axis direction, and the z-axis direction. As shown in FIG. 3, the unit cell 1 has the same length a in each of the x-axis direction, the y-axis direction, and the z-axis direction. In the cell combination 10 shown in FIG. 1, the unit cells 1 are combined together to form a length l in the x-axis direction, a length m in the y-axis direction, and a length n in the z-axis direction.

Figure 4:
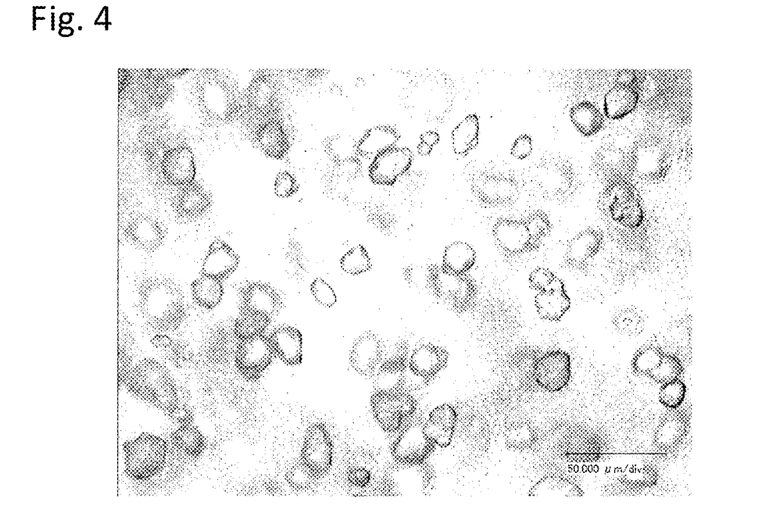
FIG. 4 is an optical micrograph of a powder-dispersed composite material having a content of powder of 5% by volume.
Figure 5:
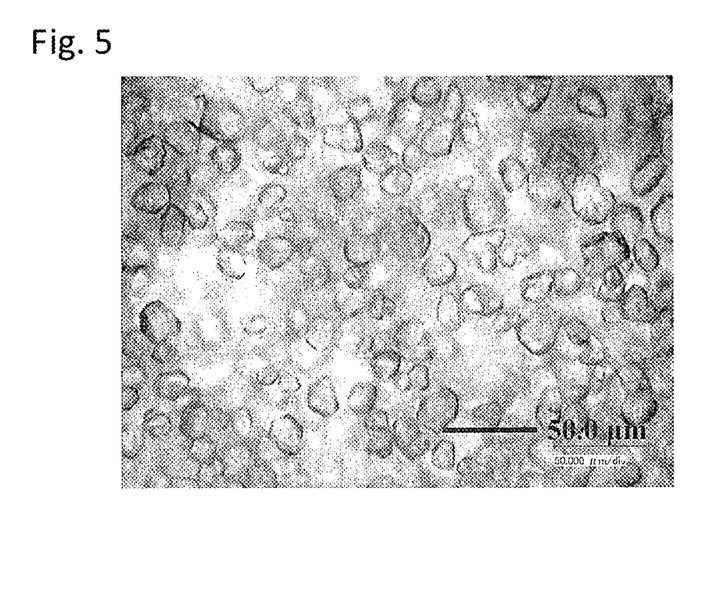
FIG. 5 is an optical micrograph of a powder-dispersed composite material having a content of powder of 20% by volume.

FIG. 4 is an optical micrograph of an example of a powder-dispersed composite material having a content of powder of 5% by volume. FIG. 5 is an optical micrograph of an example of a powder-dispersed composite material having a content of powder of 20% by volume. In these cases, alumina powder is used as powder and polyvinyl chloride (PVC) is used as a medium. As shown in FIGS. 4 and 5, there are observed powder in which powder particles are in contact with each other and powder in which powder particles are out of contact with each other. In the present invention, a mass of powder in which powder particles are in contact with each other is evaluated as an agglomerate. On the other hand, powder in which powder particles are out of contact with each other is evaluated as disperse powder.

Figure 6:
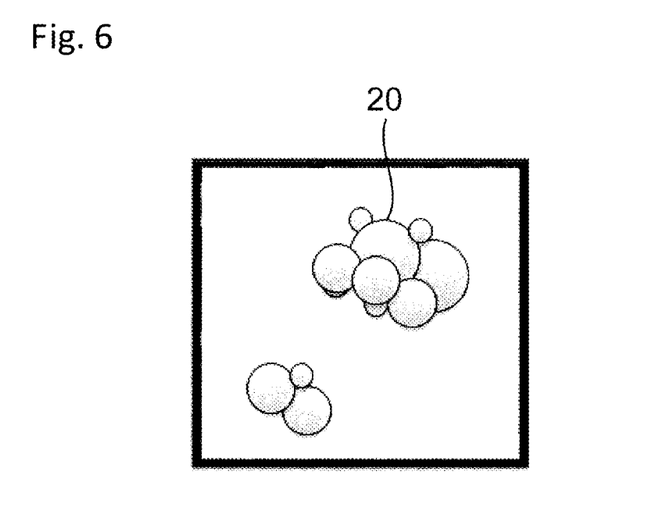
FIG. 6 is a perspective view showing powder agglomerates.
Figure 7:
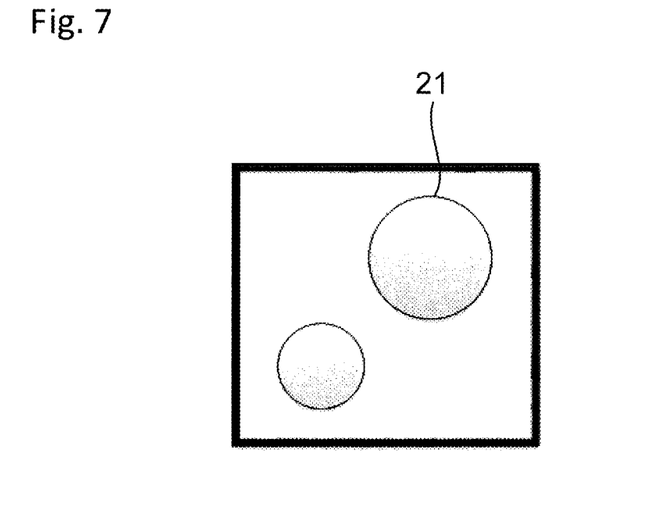
FIG. 7 is a perspective view showing powder agglomerate models in the present invention.

In the method for measuring a dielectric constant according to the present invention, each agglomerate 20 shown in FIG. 6 is treated as an agglomerate model 21 as shown in FIG. 7. Specifically, the agglomerate 20 is treated as a single powder particle (agglomerate model 21) having a larger diameter than single powder particles forming the agglomerate 20.

As shown in FIG. 1, in the cell combination 10, each unit cell 1 is considered to consist of a single element and a powder element or a medium element is assigned to each unit cell 1. In FIG. 1, black unit cells 1 represent unit cells 1 to which powder elements are assigned, while white unit cells 1 represent unit cells 1 to which medium elements are assigned.

In the present invention, the number-based median particle diameter $D_{50}$, the maximum diameter $D_{max}$, the minimum diameter $D_{min}$, and the geometric standard deviation $\sigma_g$ in a particle diameter distribution of powder in an unagglomerated state are previously measured. The particle diameter distribution of powder in an unagglomerated state can be determined, for example, by measuring the particle diameter distribution of powder particles in powder form. The particle diameter distribution in powder form can be measured, for example, by a laser diffraction particle size distribution analyzer or observation with a microscope or the like. In determining the particle diameter by observation with a microscope or the like, the Green diameter in a predetermined direction can be defined as the particle diameter.

In assigning a powder element or a medium element to each unit cell 1 of the cell combination 10, the powder element or the medium element is assigned to each unit cell 1 in consideration of the above number-based median particle diameter $D_{50}$, maximum diameter $D_{max}$, minimum diameter $D_{min}$, and geometric standard deviation $\sigma_g$ in the particle diameter distribution and the content of powder in the powder-dispersed composite material.

As for the cell combination 10 in which powder elements or medium elements are assigned to the unit cells 1 in the above manner, its dielectric constant is calculated. In calculating the dielectric constant of the cell combination 10 in the present invention, the cell combination 10 is assumed as a laminate in which layers having a thickness d in the z-axis direction are combined and layered in the z-axis direction.

Figure 2:
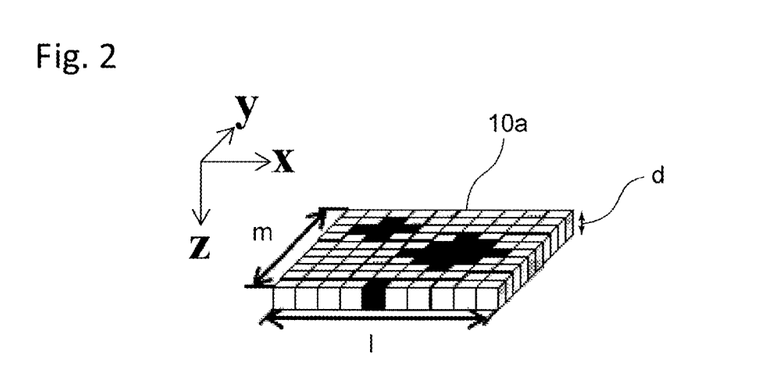
FIG. 2 is a perspective view for illustrating a layer assumed in determining the dielectric constant of the cell combination in the present invention.

FIG. 2 is a perspective view showing a layer constituting part of the above laminate. As shown in FIG. 2, the layer 10a has a thickness d in the z-direction. Furthermore, its length in the x-direction is l and its length in the y-direction is m. When the layers 10a shown in FIG. 2 are combined in the z-axis direction, the cell combination 10 shown in FIG. 1 is formed.

No particular limitation is placed on the thickness d of the layer 10a, but d represented by the following formula is preferably used.

$$d = (D_4 \sigma_g)/2(1+P_f)$$

$D_4$: volume mean diameter (µm)

$P_f$: volume content of powder (within a range of 0 to 1)

The volume mean diameter $D_4$ and the geometric standard deviation $\sigma_g$ are defined by the following formulas.

$$D_4 = D_{4,D}(1-V_{aN}/100) + D_{4,A}V_{aN}/100$$

$$\sigma_g = \sigma_{g,D}(1-V_{aN}/100) + \sigma_{g,A}V_{aN}/100$$

Suffix D: group of unagglomerated (dispersed) powder

Suffix A: group of agglomerated powder $V_{aN}$: percentage of number of agglomerates The capacitance $C_{Layer,h}$ of the layer 10a (the capacitance of the h-th layer) can be represented by the following Formula 1.

[Math. 1]

$$C_{Layer,h} = \left\{ \sum_{j=1}^{\lfloor m/a \rfloor} \sum_{i=1}^{\lfloor l/a \rfloor} \left( \sum_{k=1}^{\lfloor d/a \rfloor} \frac{1}{\varepsilon_{ijk} \varepsilon_0 a} \right)^{-1} \right\}^{-1} \quad \text{Formula 1}$$

$\varepsilon_0$: dielectric constant of vacuum (F/m)

Note that the unit of the lengths l, m, and n is μm.

Figure 8:
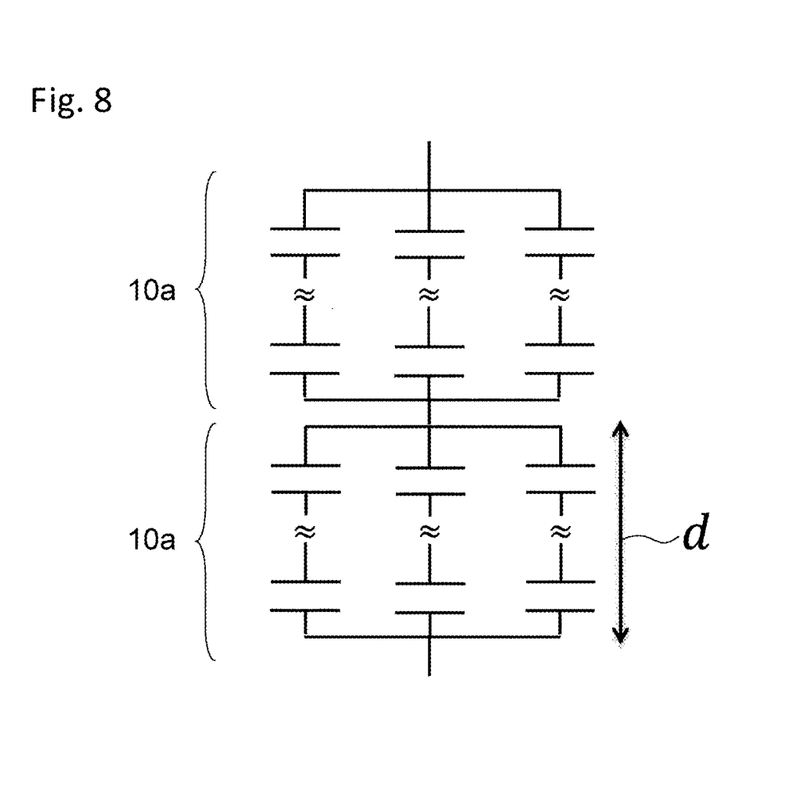
FIG. 8 is a diagram showing an electric circuit model of a laminate of layers constituting the cell combination.

FIG. 8 is a diagram showing an electric circuit model of a laminate of layers 10a constituting the cell combination 10. The relative dielectric constant $\varepsilon_{Total}$ of the cell combination 10 can be determined by assigning the capacitance $C_{Layer,h}$ of each layer 10a to the following Formula 2.

[Math. 2]

$$\varepsilon_{Total} = \frac{1}{\varepsilon_0} \cdot \frac{n}{lm} \cdot \left( \sum_{h=1}^{\lfloor n/d \rfloor} C_{Layer,h} \right)^{-1} \quad \text{Formula 2}$$

According to the present invention, the relative dielectric constant of the powder-dispersed composite can be calculated by determining the relative dielectric constant $\varepsilon_{Total}$ of the cell combination 10 in the above manner.

Although an arbitrary value can be used as the length a of the unit cell, a value of a determined by the following formula is preferably used.

$a = (D_{50}/\beta \sigma_g)$

β: fitting parameter

<Method for Determining Fitting Parameter β>

An optimal fitting parameter β was determined under the conditions shown in Table 1. The fitting parameter β was changed within a range of 2 to 30.

TABLE 1

| System Size | l (x-direction) | 30 (μm) |
|---|---|---|
| | m (y-direction) | 30 (μm) |
| | n (z-direction) | 30 (μm) |
| Unit Cell Length | a | $D_{50}/\beta \sigma g$ (β = 2~30) |
| Particle Diameter Distribution | Max. Diameter Dmax | 1.69 (μm) |
| | Min. Diameter Dmin | 0.35 (μm) |
| | Median Diameter $D_{50}$ | 0.77 (μm) |
| | Geom. Standard Deviation | 1.47 (—) |
| Dielectric Constant of Vacuum | | 8.854 × 10$^{-12}$ (Fm$^{-1}$) |
| Dielectric Constant of Medium | | 2.227 (—) |
| Dielectric Constant of Particles | | 100 (—) |
| Volume Content of Particles | | 10 (%) |

Figure 9:
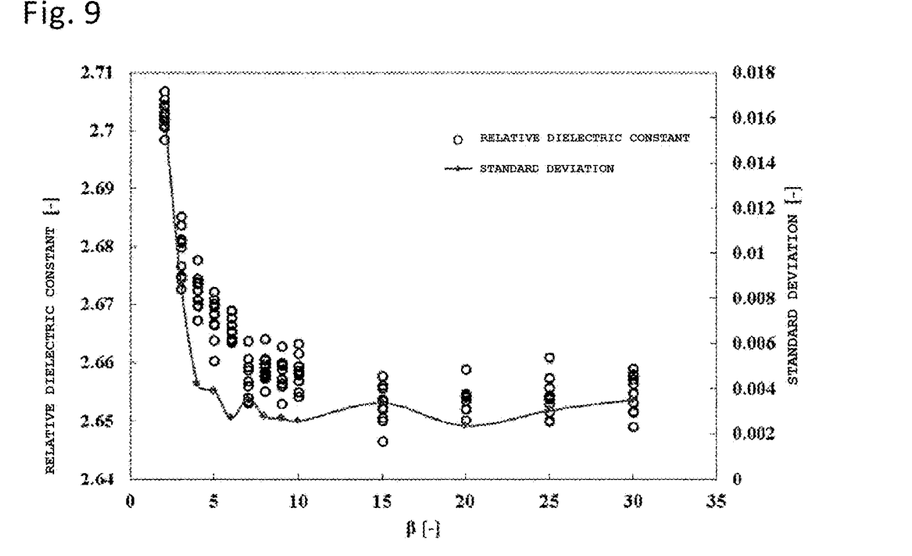
FIG. 9 is a graph showing results of simulation for determining the length of the unit cell.

FIG. 9 is a graph showing results of simulation for determining the length a of the unit cell. As shown in FIG. 9, the standard deviation of the relative dielectric constant is constant when the fitting parameter β is within a range of 10 to 30. To reduce the computational load, the value 10 was adopted as the fitting parameter β in the simulations below.

Next, an optimal number of unit cells was determined under the conditions shown in Table 2. The number of unit cells was changed within a range of 100 to 2000. Furthermore, the volume content of powder was changed within a range of 0 to 15% by volume.

TABLE 2

| Number of Cells | l/a (x-direction) | 100~2000 (—) |
|---|---|---|
| | m/a (y-direction) | 100~2000 (—) |
| | n/a (z-direction) | 100~2000 (—) |
| Unit Cell Length | a | $D_{50}/10\sigma g$ |
| Particle Diameter Distribution | Max. Diameter Dmax | 1.69 (μm) |
| | Min. Diameter Dmin | 0.35 (μm) |
| | Median Diameter $D_{50}$ | 0.77 (μm) |
| | Geom. Standard Deviation | 1.47 (—) |
| Dielectric Constant of Vacuum | | 8.854 × 10$^{-12}$ (Fm$^{-1}$) |
| Dielectric Constant of Medium | | 134 (—) |
| Dielectric Constant of Particles | | 7.4 (—) |
| Volume Content of Particles | | 0~15 (%) |

Figure 10:
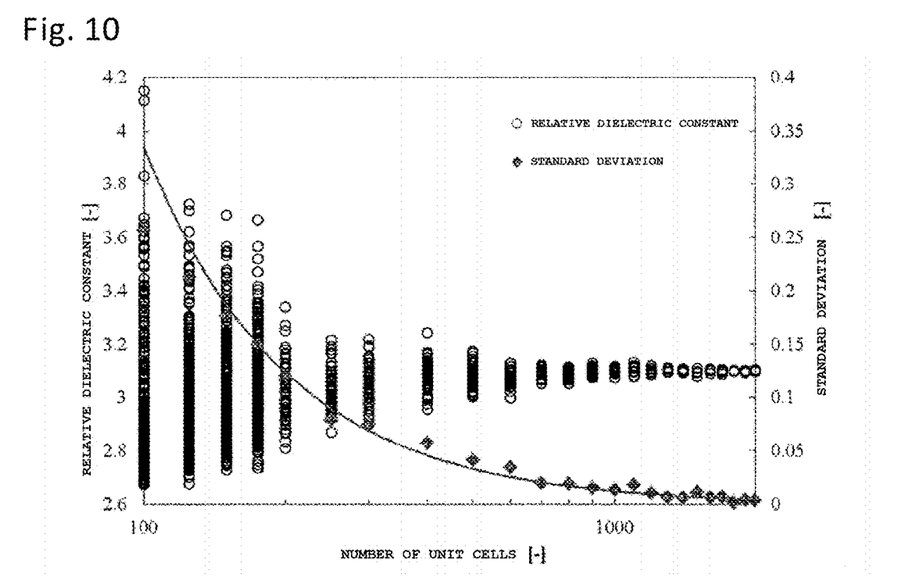
FIG. 10 is a graph showing results of simulation for determining the number of unit cells.

FIG. 10 is a graph showing results of simulation for determining the number of unit cells. As shown in FIG. 10, when the number of unit cells is 1000 or more, the standard deviation of the relative dielectric constant is around 0.01. In the simulations below, the number of unit cells was set at 1500 on the safe side.

<Another Method for Determining Fitting Parameter β>

In the above method for determining the fitting parameter β, the fitting parameter β is determined within a range of values where the standard deviation of the relative dielectric constant is constant, i.e., within a range of values where variations in relative dielectric constant are sufficiently small. However, in the case of a system in which the difference in dielectric constant between powder and a medium is not so large, it may be difficult to examine the fitting parameter β based on variations in relative dielectric constant. As another method for determining the fitting parameter β, a method for determining the fitting parameter β within a range of values where variations in calculated volume content of powder are sufficiently small may be adopted.

Figure 11:
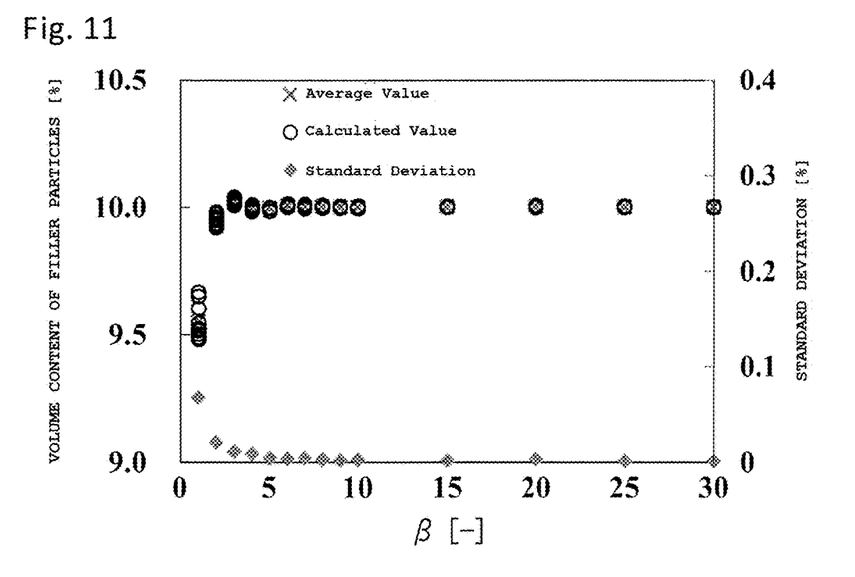
FIG. 11 is a graph showing simulation results of calculated volume contents of powder and their standard deviations.

FIG. 11 is a graph showing simulation results of calculated volume contents of powder and their standard deviations. As shown in FIG. 11, the standard deviation of the volume content is small when the fitting parameter β is within a range of 10 to 30. Therefore, like the method described previously, the value 10 can be adopted as the fitting parameter β.

<Production of Powder-Dispersed Composite Material and Measurement of Relative Dielectric Constant of Powder-Dispersed Composite Material>

A powder-dispersed composite material is produced and its relative dielectric constant is measured.

<Volume Content Va % of Agglomerates and Average Number Na of Primary Powder Particles Forming Agglomerates>

The produced powder-dispersed composite material is measured in terms of the volume content Va % of agglomerates in the whole powder and the average number Na of primary powder particles forming the agglomerates by a technique, such as image analysis.

Figure 12:
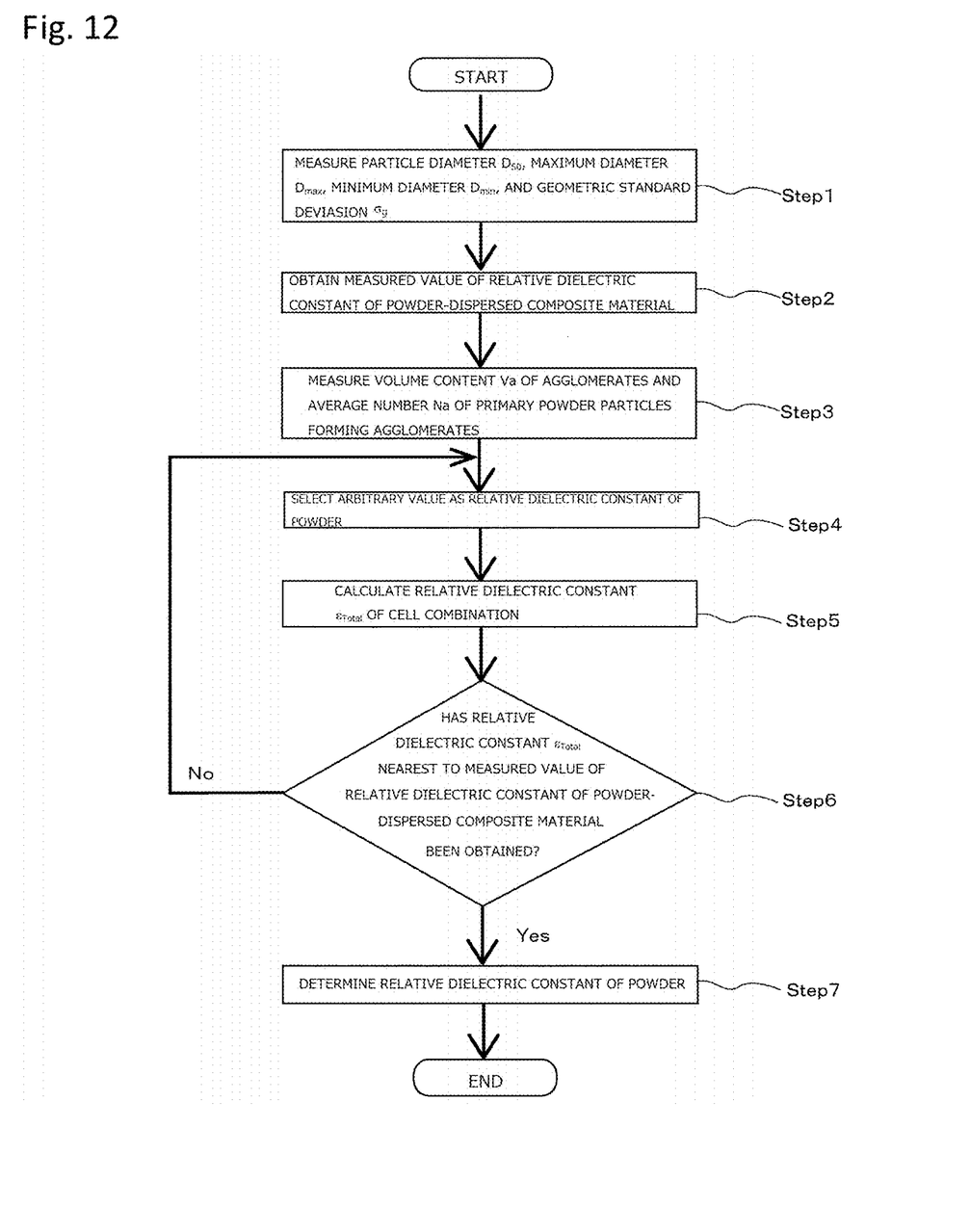
FIG. 12 is a flowchart showing an example of a method for measuring a dielectric constant according to the present invention.

FIG. 12 is a flowchart showing an example of a method for measuring a dielectric constant according to the present invention.

(Step 1)

The number-based median particle diameter $D_{50}$, the maximum diameter $D_{max}$, the minimum diameter $D_{min}$, and the geometric standard deviation $\sigma_g$ in a particle diameter distribution of powder in an unagglomerated state are measured.

(Step 2)

The relative dielectric constant of the powder-dispersed composite material is measured to obtain a measured value of the relative dielectric constant of the powder-dispersed composite material.

(Step 3)

The produced powder-dispersed composite material is measured in terms of the volume content Va % of agglomerates in the whole powder and the average number Na of primary powder particles forming the agglomerates. The order of Step 2 and Step 3 may be reversed.

(Step 4)

An arbitrary value is selected as the relative dielectric constant of the powder.

(Step 5)

The relative dielectric constant $\varepsilon_{Total}$ of the cell combination is calculated using the selected relative dielectric constant of the powder, the values of Va and Na, the number-based median particle diameter $D_{50}$, maximum diameter $D_{max}$, minimum diameter $D_{min}$, and geometric standard deviation $\sigma_g$ in the particle diameter distribution of the powder in an unagglomerated state and the content of the powder in the powder-dispersed composite material.

(Step 6)

A comparison is made between the calculated relative dielectric constant $\varepsilon_{Total}$ and the measured value of the relative dielectric constant and (Step 4) and (Step 5) are repeated until it is confirmed that a relative dielectric constant $\varepsilon_{Total}$ nearest to the measured value of the relative dielectric constant has been obtained.

(Step 7)

A relative dielectric constant of the powder is determined which gives the relative dielectric constant $\varepsilon_{Total}$ of the cell combination nearest to the measured value of the relative dielectric constant of the powder-dispersed composite material.

The relative dielectric constant of powder in a powder-dispersed composite material can be measured in the above manner.

(Measurement of Relative Dielectric Constant of Powder in Powder-Dispersed Composite Material)

<Sample 1>

In Sample 1, a powder-dispersed composite material was produced using spherical silica particles as powder and polypropylene glycol (PPG) as a medium. The volume content of powder in the composite material was set at 30%. The obtained powder-dispersed composite material was measured in terms of relative dielectric constant with an LCR meter. The measured relative dielectric constant is shown as Dielectric Constant of Composite Material in Table 3. Furthermore, when the obtained powder-dispersed composite material was observed by image analysis, no agglomerate was found. Therefore, the volume content Va % of agglomerates in the whole powder of the powder-dispersed composite material was determined to be 0% and the average number Na of primary powder particles forming agglomerates was determined to be 1.

The number-based median particle diameter $D_{50}$, the maximum diameter $D_{max}$, the minimum diameter $D_{min}$, and the geometric standard deviation $\sigma_g$ in a particle diameter distribution of unagglomerated spherical silica particles are as shown in Table 3. When the relative dielectric constant of the medium was measured with an LCR meter, it was 5.00.

An arbitrary value was selected as a relative dielectric constant of the spherical silica particles and simulation was performed under the conditions shown in Table 3, thus determining the relative dielectric constant $\varepsilon_{Total}$ of the cell combination. This simulation was repeatedly performed and the relative dielectric constant of the spherical silica particles giving values nearest to the above measured value of the relative dielectric constant of the powder-dispersed composite material was determined. As a result, the relative dielectric constant of the spherical silica particles was 3.96.

TABLE 3

| Number of Cells | l/a (x-direction) | 1500 (—) |
|---|---|---|
| | m/a (y-dierction) | 1500 (—) |
| | n/a (z-direction) | 1500 (—) |
| Unit Cell Length | a | $D_{50}/10\sigma_g$ |
| Particle Diameter Distribution | Max. Diameter $D_{max}$ | 1.32 (μm) |
| | Min. Diameter $D_{min}$ | 0.71 (μm) |
| | Median Diameter $D_{50}$ | 0.97 (μm) |
| | Geometric Standard Deviation | 1.1 (μm) |
| Dielectric Constant or Vacuum | | $8.854 \times 10^{-12}$ (Fm$^{-1}$) |
| Dielectric Constant of Medium | | 5.00 (—) |
| Dielectric Constant of Composite Material | | 4.67 (—) |
| Volume Content of Particles | | 30 (%) |

<Sample 2>

In Sample 2, spherical silica particles subjected to surface treatment (hereinafter, referred to as "surface-treated silica particles") were used as powder. The surface-treated silica particles were produced by treating the spherical silica particles used in Sample 1 with n-propyltrimethoxysilane as a surface treating agent. Specifically, 10 parts by mass of surface treating agent was used relative to 100 parts by mass of spherical silica particles. The surface treating agent was added in dry form to spherical silica particles being stirred and they were mixed with stirring for 10 minutes after the addition and then dried at 120° C. for 15 hours, thus obtaining surface-treated silica particles.

A powder-dispersed composite material was produced in the same manner as in Sample 1 except for the above. The obtained powder-dispersed composite material was measured in terms of relative dielectric constant with an LCR meter. The measured relative dielectric constant is shown as Dielectric Constant of Composite Material in Table 4.

When the obtained powder-dispersed composite material was observed by image analysis, no agglomerate was found. Therefore, the volume content Va % of agglomerates in the whole powder of the powder-dispersed composite material was determined to be 0% and the average number Na of primary powder particles forming agglomerates was determined to be 1.

The number-based median particle diameter $D_{50}$, the maximum diameter $D_{max}$, the minimum diameter $D_{min}$, and the geometric standard deviation $\sigma_g$ in a particle diameter distribution of unagglomerated surface-treated silica particles are as shown in Table 4. When the relative dielectric constant of the medium was measured with an LCR meter, it was 5.01.

An arbitrary value was selected as a relative dielectric constant of the surface-treated silica particles and simulation was performed under the conditions shown in Table 4, thus determining the relative dielectric constant $\varepsilon_{Total}$ of the cell combination. This simulation was repeatedly performed and the relative dielectric constant of the surface-treated silica particles giving values nearest to the above measured value of the relative dielectric constant of the powder-dispersed composite material was determined. As a result, the relative dielectric constant of the surface-treated silica particles was 4.15.

TABLE 4

| Number of Cells | l/a (x-direction) | 1500 | (—) |
| --- | --- | --- | --- |
| | m/a (y-dirsction) | 1500 | (—) |
| | n/a (z-direction) | 1500 | (—) |
| Unit Cell Length | a | $D_{50}/10\sigma g$ | |
| Particle Diameter Distribution | Max. Diameter $D_{max}$ | 1.32 | (μm) |
| | Min. Diameter $D_{min}$ | 0.71 | (μm) |
| | Median Diameter $D_{50}$ | 0.97 | (μm) |
| | Geometric Standard Deviation | 1.1 | (μm) |
| Dielectric Constant or Vacuum | | $8.854 \times 10^{-12}$ | $(Fm^{-1})$ |
| Dielectric Constant of Medium | | 5.01 | (—) |
| Dielectric Constant of Composite Material | | 4.74 | (—) |
| Volume Content of Particles | | 30 | (%) |

As seen from the above, the present invention enables the measurement of the relative dielectric constant of powder in a powder-dispersed composite material. In addition, the present invention also enables the measurement of the relative dielectric constant of surface-treated powder.

REFERENCE SIGNS LIST

1 . . . unit cell
10 . . . cell combination
10a . . . layer
20 . . . agglomerate
21 . . . agglomerate model

The invention claimed is:

1. A method for measuring a dielectric constant of powder in a powder-dispersed composite material containing the powder dispersed in a medium, the method comprising:
    measuring a number-based median particle diameter $D_{50}$, a maximum diameter $D_{max}$, a minimum diameter $D_{min}$, and a geometric standard deviation $\sigma_g$ in a particle diameter distribution of the powder in an unagglomerated state;
    measuring a relative dielectric constant of the powder-dispersed composite material, a volume content Va % of agglomerates in the whole powder of the powder-dispersed composite material, and an average number Na of primary particles forming the agglomerates;
    assuming the powder-dispersed composite material as a cell combination in which unit cells having the same length a in each of an x-axis direction, a y-axis direction, and a z-axis direction are combined together in the x-axis direction, the y-axis direction, and the z-axis direction and which has a length l in the x-axis direction, a length m in the y-axis direction, and a length n in the z-axis direction;
    considering that each of the unit cells of the cell combination is constituted by a single powder element or a single medium element, and creating the cell combination in which the powder element or the medium element is assigned to each of the unit cells in consideration of the number-based median particle diameter $D_{50}$, the maximum diameter $D_{max}$, the minimum diameter $D_{min}$, and the geometric standard deviation $\sigma_g$ in the particle diameter distribution and a content of the powder in the powder-dispersed composite material; and
    assuming the cell combination as a laminate in which layers having a thickness d in the z-axis direction are combined and layered in the z-axis direction, and determining a relative dielectric constant of the powder in the powder-dispersed composite material from a relational expression of a relative dielectric constant $\varepsilon_{Total}$ of the cell combination determined by assigning a capacitance $C_{Layer,h}$ of each of the layers represented by Formula 1 below to Formula 2 below and a measured value of the relative dielectric constant of the powder-dispersed composite material $$C_{Layer,h} = \left\{ \sum_{j=1}^{\lfloor m/a \rfloor} \sum_{i=1}^{\lfloor l/a \rfloor} \left( \sum_{k=1}^{\lfloor d/a \rfloor} \frac{1}{\varepsilon_{ijk}\varepsilon_0 a} \right)^{-1} \right\}^{-1} \quad \text{Formula 1}$$

$\varepsilon_0$: dielectric constant of vacuum (F/m)

$$\varepsilon_{Total} = \frac{1}{\varepsilon_0} \cdot \frac{n}{lm} \cdot \left( \sum_{h=1}^{\lfloor n/d \rfloor} C_{Layer,h} \right)^{-1} \quad \text{Formula 2}$$

2. The method for measuring a dielectric constant of powder in a powder-dispersed composite material according to claim 1, wherein the length a of the unit cell is $a=(D_{50}/\beta\sigma_g)$ and a fitting parameter $\beta$ thereof is selected within a range of values where determination results of the relative dielectric constant $\varepsilon_{Total}$ have a constant standard deviation or within a range of values where variations in calculated volume content of the powder are sufficiently small.

3. The method for measuring a dielectric constant of powder in a powder-dispersed composite material according to claim 1, wherein the powder is surface-treated powder.

* * * * *